United States Patent [19]
Addis

[11] Patent Number: 6,152,948
[45] Date of Patent: Nov. 28, 2000

[54] SUTURE-FREE CLAMP AND SEALING PORT AND METHOD OF USE

[75] Inventor: Bruce Addis, Redwood City, Calif.

[73] Assignee: Embol-X, Inc., Mountain View, Calif.

[21] Appl. No.: 09/472,763

[22] Filed: Dec. 27, 1999

Related U.S. Application Data

[63] Continuation of application No. 09/209,561, Dec. 11, 1998, Pat. No. 6,024,755.

[51] Int. Cl.⁷ .................................................. A61B 17/00
[52] U.S. Cl. ............................................................. 606/213
[58] Field of Search .................................. 606/213, 232, 606/104, 215, 151; 604/11, 115, 116, 167, 169; 600/32

[56] References Cited

U.S. PATENT DOCUMENTS

| | | | |
|---|---|---|---|
| 5,545,179 | 8/1996 | Williamson, IV | 606/213 |
| 5,634,911 | 6/1997 | Hermann et al. | 604/256 |
| 5,814,073 | 9/1998 | Bonutti | 606/232 |
| 5,840,078 | 11/1998 | Yerys | 606/151 |

*Primary Examiner*—Michael Buiz
*Assistant Examiner*—Hoa B. Trinh
*Attorney, Agent, or Firm*—Lyon & Lyon LLP

[57] ABSTRACT

A suture-free clamp for sealing body tissue during introduction of medical devices, such as a cannula, aspirator, stent, endoscope, and pressure monitor. The clamp may be used in a patient's vascular tissues, such as the right atrium and the aorta. The clamp comprises a generally cone-shaped housing which includes a lumen for receiving a medical device, and a collar having a central opening for passage of a medical device, the collar connected to a proximal end of the housing by a plurality of struts. The proximal end of the housing and the collar each has an annular surface. The two surfaces are opposed, and are operable to clamp tissue therebetween, and to thereafter release the tissue by releasing the clamp. Methods are also disclosed for using the suture-free clamp for sealing body tissues during introduction of a medical device.

22 Claims, 3 Drawing Sheets

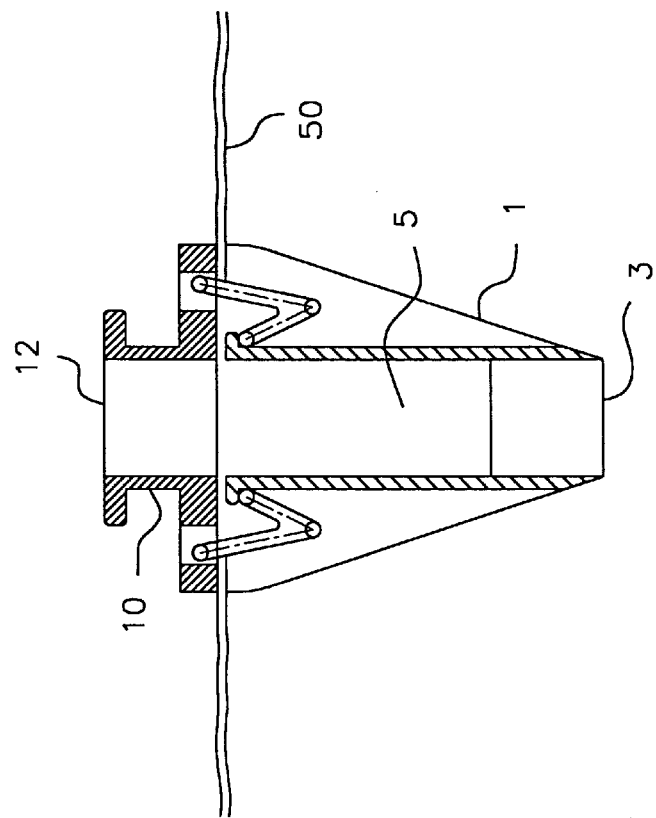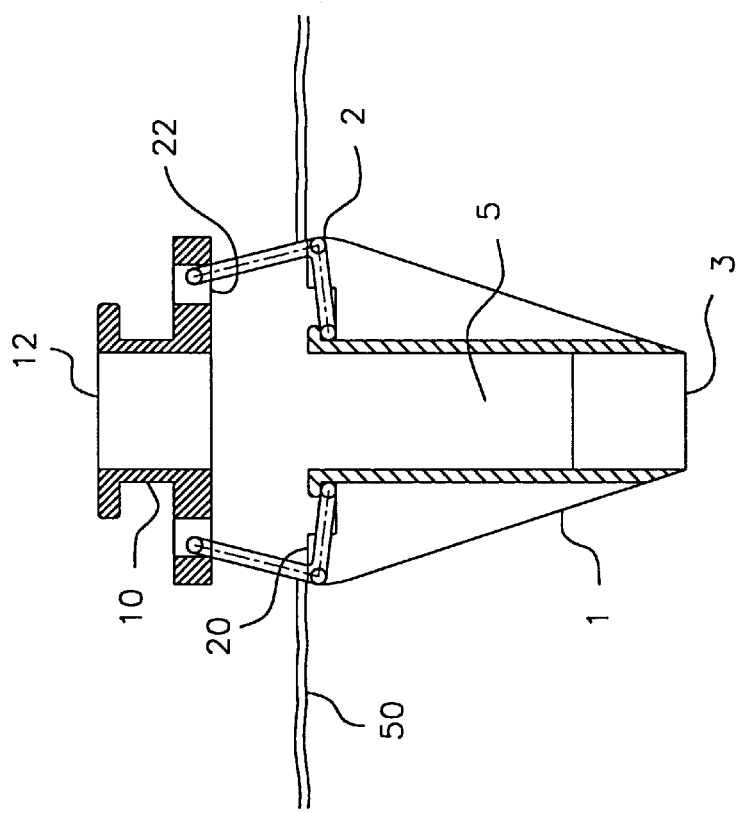
FIG. 2A
FIG. 2B

SUTURE-FREE CLAMP AND SEALING PORT AND METHOD OF USE

This is a continuation of U.S. application Ser. No. 09/209,561, filed Dec. 11, 1998, now U.S. Pat. No. 6,024,755, incorporated herein by reference in its entirety.

FIELD OF THE INVENTION

The present invention relates generally to using a clamp for sealing a patient's body tissue during introduction of medical devices, such as cannula, endoscope, aspirator, and pressure monitor. More specifically, the invention relates to a suture-free clamp for sealing atrial tissue during cardiothoracic surgeries, and providing a port in which medical devices can be inserted through the clamp without injuring the atrial tissue.

BACKGROUND OF THE INVENTION

During conventional or endoscopic surgical procedures, such as open cholecystectomy or laparoscopic oophorectomy, introduction of medical devices, such as a cannula, stent, endoscope, aspirator, or pressure monitor, into a patient's body tissue often requires an incision on the body tissue. Sutures are generally required to establish hemostasis and secure the medical device onto the body tissue. Repositioning of the medical device requires loosening or removing the sutures and re-tightening or replacing the existing sutures with new ones.

During various cardiothoracic surgeries, such as coronary artery bypass graft, heart valve repair, septal defect repair, pulmonary thrombectomy, thoracic aortic aneurysm repair, atherectomy, and removal of atrial myxoma, cardiopulmonary bypass and cardiac arrest are often required. Cardiac arrest is generally achieved by infusing cardioplegic solution through an arterial catheter into the coronary ostia or through an atrial catheter into the coronary sinus. After the myocardium is paralyzed, cardiopulmonary bypass is required to support the peripheral circulation. Deoxygenated blood is usually drained through a venous cannula from the right atrium, superior vena cava, or inferior vena cava to a bypass-oxygenator, and oxygenated blood is returned from the bypass-oxygenator to the ascending aorta through an arterial cannula to perfuse peripheral organs.

The right atrial appendage is often incised to allow insertion of the venous return cannula or cardioplegic catheter during cardiothoracic surgeries. After the cannula is placed in the right atrium, a purse string suture is often placed on the atrial tissue around the incision site to achieve hemostasis, and the suture pulled tightly against the rigid cannula to secure the cannula. Disadvantages associated with the present technique are that (1) placing sutures on the atrium is time consuming, (2) repositioning of the cannula requires manipulating sutures on the atrial tissue, i.e. loosening and re-tightening sutures around the cannula, and (3) delicate atrial structures may be damaged due to suture placement and manipulation.

Methods and devices are therefore needed for sealing body tissues during introduction of other medical devices, that eliminate the need for sutures and reduce the risk of tissue injury during manipulation of other medical devices.

SUMMARY OF THE INVENTION

The present invention provides a suture-free clamp for sealing body tissues during introduction of a medical device. The clamp may be used in either open or minimally invasive procedures. The clamp can be made of molded plastic or metal injection molded metal.

In a preferred embodiment, the clamp comprises a generally cone-shaped housing and a collar operably connected to a proximal end of the housing by a plurality of struts. The housing has an outer surface, a large diameter proximal end, a smaller diameter distal end, and a lumen therebetween. The outer surface is generally smooth and tapered from the proximal end to the distal end, thereby facilitating insertion of the clamp into a body tissue. The collar has a central opening that is aligned with the lumen of the housing and is adapted for receiving a medical device. The collar further includes an annular surface which surrounds the opening and is operable to engage an annular surface of the proximal end of the housing to clamp body tissue therebetween. The tissue is released by releasing the clamp.

In another embodiment, the struts may have a pivoting internal joint and are pivotally connected to the housing and the collar. In still another embodiment, the struts are located and operate within a plurality of distally extending slots which are included in the housing.

In still another embodiment, the lumen of the housing further includes a hemostatic valve to reduce hemorrhaging when the clamp is used, especially in a patient's blood vessel, such as an aorta.

In still another embodiment, the housing and the collar may be constructed so that they snap together, or are bonded. The clamp may also be made from a smooth material having a spring type elastic property that provides the clamp force.

The invention also provides methods for sealing body tissues during introduction of a medical device using the suture-free clamp described above. An incision is made in a body tissue, and the distal end of the housing is introduced through the incision. The edges of the incision are stretched as the tissue advances along the widening surface of the cone, until the tissue is positioned against the annular surface of the housing. The collar is pushed distally to engage the tissue against the annular surface of the collar, so that the tissue is clamped between the annular surface of the housing and the collar, thereby sealing the body tissue. A medical device, such as a cannula, is introduced through the opening of the collar and the lumen of the housing, and advanced into the body. Alternatively, the medical device may be inserted through the collar and housing before clamping the introducer to the body tissue. In this way, the medical device can be manipulated through the lumen of the housing and repositioned inside the body tissue without disturbing the tissue, thereby reducing risk of injury to the tissue.

BRIEF DESCRIPTION OF THE DRAWINGS

FIG. 2A depicts the suture-free clamp of FIG. 1A engaging a patient's body tissue.

FIG. 2B depicts the suture-free clamp of FIG. 1A fully clamping the body tissue.

DETAILED DESCRIPTION

The devices and methods disclosed herein are particularly useful in cardiothoracic surgeries in which multiple incision sites are required for insertion of arterial and venous return cannula. Using the suture-free clamp would facilitate introduction of the cannulas more efficiently than the conventional methods which require sutures. Less damage would occur using the clamp on the delicate vascular tissues, such as the right atrium.

Figure 1D:
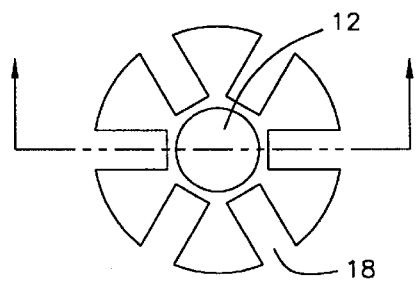
FIG. 1D depicts a top view of the suture-free clamp shown in FIG. 1A.
Figure 1A:
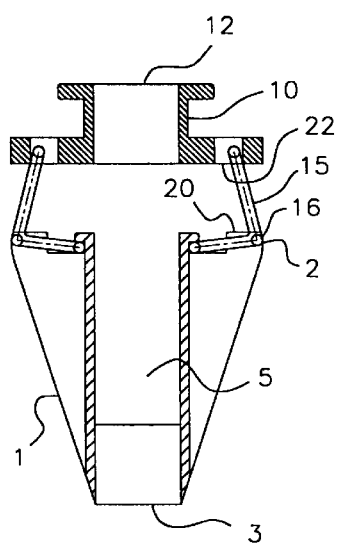
FIG. 1A depicts a cross-sectional view of a first embodiment of a suture-free clamp in an unclamped position according to the present invention.
Figure 1B:
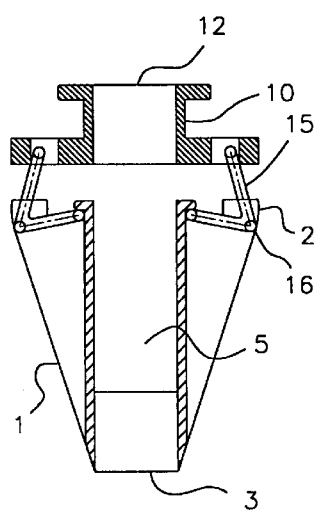
FIG. 1B depicts a cross-sectional view of the suture-free clamp of FIG. 1A in a midway clamped position.
Figure 1C:
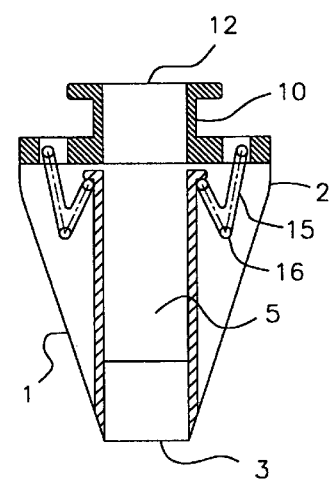
FIG. 1C depicts a cross-sectional view of the suture-free clamp of FIG. 1A in a fully clamped position.

FIGS. 1A, 1B, and 1C depict cross-sectional views of a first embodiment of the suture-free clamp in an unclamped, midway clamped, and fully clamped position respectively. Housing 1 has proximal end 2, distal end 3, and lumen 5. The housing is cone-shaped, and its outer surface tapered from proximal end 2 to distal end 3. Lumen 5 is adapted for receiving a medical device. The proximal end is connected to collar 10 through struts 15. The clamp may include 1, 2, 3, 4, 5, 6 or more struts. The struts, having internal joint 16, are flexibly connected to the housing and the collar, optionally connected through a pivot. The struts can be made from a flexible material, e.g., polyvinylidene fluoride (PVDF), or spring metals, e.g., stainless steel. These materials can be thermally set or mechanically formed into the desired shape. In their undeployed state, as shown in FIG. 1A, these struts are bent such that they would create a spring tension pulling the collar against the proximal end of the housing. The collar has opening 12, which aligns with lumen 5 of the housing, and together with the lumen forms a sealed port for introduction of medical devices. Annular surface 22, which surrounds opening 12, is operable to engage annular surface 20 of the housing to clamp tissue in between, as shown in FIG. 1C. When the surgeon desires to release the tissue, the collar is released from the housing, and the clamp returned to the unclamped position as depicted in FIG. 1A.

Figure 1E:
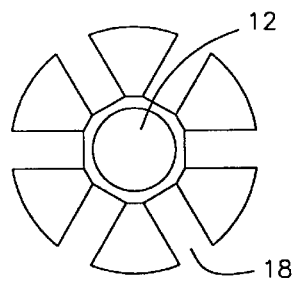
FIG. 1E depicts a top view of the suture-free clamp shown in FIG. 1B.

FIGS. 1D and 1E depict a top view of the clamp shown in FIGS. 1A and 1B respectively. A medical device can be inserted through opening 12 of the collar. Slots, 18, in which the struts are located, are evenly spaced about the circumference of the housing. The clamp may include 2, 3, 4, 5 or any other number of slots, and typically the number will correspond to the number of struts.

Figure 3:
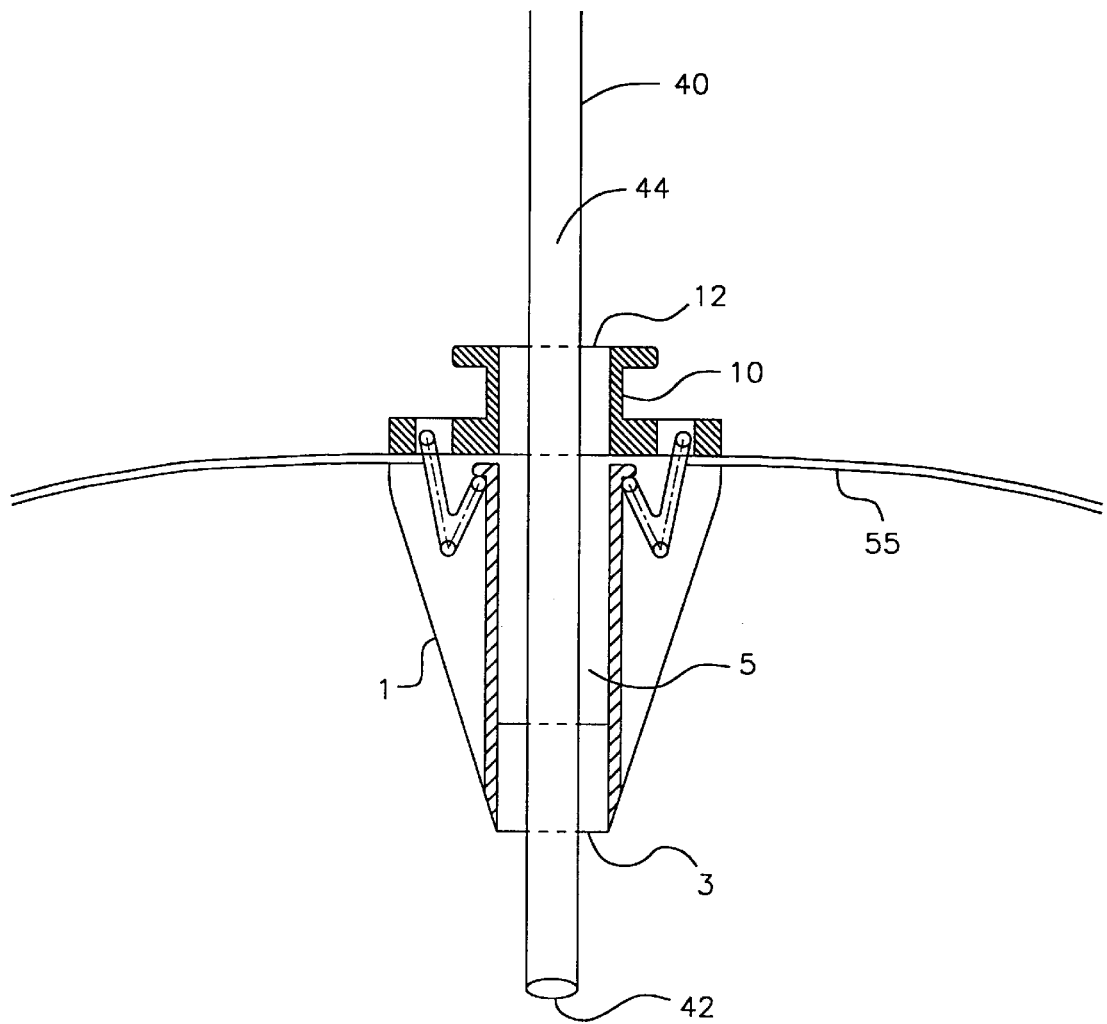
FIG. 3 depicts a cannula introduced through the suture-free clamp inserted into a patient's atrium.

The methods of using the suture-free clamp are demonstrated through FIGS. 2A, 2B, and 3. In FIG. 2A, housing 1 is shown inserted through body tissue 50 after an incision is made on the tissue. The body tissue may be a patient's abdominal wall as in laparoscopic abdominal and pelvic surgeries or a patient's vascular tissues, such as the right atrium, the aorta, the femoral artery, or the vena cava in cardiothoracic surgeries. After distal end 3 of the housing is introduced through the incision, the tissue is positioned against annular surface 20 of the housing. Collar 10 is then operated to engage the tissue against annular surface 22 of the collar, so that the tissue is clamped between surface 20 and surface 22 as shown in FIG. 2B, thereby sealing the tissue.

After the tissue is sealed by the clamp, a medical device, such as cannula, catheter, aspirator, endoscope, stent, or pressure monitor can be introduced through the opening of the collar and the lumen of the housing, and advanced into the body tissue. For example, during coronary artery bypass grafting or valve repair surgeries, the right atrium is often incised for insertion of a venous return cannula for cardiopulmonary bypass. In FIG. 3, right atrial tissue 55 is clamped between the annular surfaces of collar 10 and housing 1, thereby sealing the atrial tissue without the time-consuming placement of sutures. Cannula 40 is then introduced through opening 12 and lumen 5 into the right atrium. The cannula has a proximal end which is adapted for attachment to a bypass-oxygenator machine and lumen 44 capable for receiving deoxygenated blood from distal end 42. During cardiopulmonary bypass the cannula can easily be repositioned within the lumen of the housing without disturbing the atrial tissue, thereby reducing the risk of injury to delicate atrial tissue. After a surgeon has performed the surgery, cardiac arrest is reversed and cardiopulmonary bypass is discontinued. The venous return cannula is easily removed from the clamp. The clamp is easily removed by releasing the collar to disengage atrial tissue, and then removing the housing from the incision.

The length of the housing of the suture-free clamp is generally between 0.3 and 2.0 inches, preferably approximately 0.75 inches. The outer diameter of the proximal end of the housing is generally between 0.4 and 1 inches, preferably approximately 0.75 inches. The outer diameter of the distal end of the housing is generally between 0.1 and 0.75 inches, preferably approximately 0.5 inches. The inner diameter of the lumen of the housing is generally between 0.1 and 0.75 inches, preferably approximately 0.4 inches. The length of the collar is generally between 0.25 and 0.75 inches, preferably approximately 0.5 inches. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A clamp for sealing tissues during introduction of a medical device, comprising:

a generally cone-shaped housing having an outer surface, a proximal end, a distal end, wherein the diameter of said proximal end is larger than the diameter of said distal end, and a lumen therebetween, the lumen adapted to receive a medical device for introduction through body tissues, the outer surface of the housing being generally smooth and tapered from the proximal to the distal end, the proximal end of the housing having an annular surface which lies in a plane substantially perpendicular to the longitudinal axis of the lumen; and a collar operably connected to the proximal end of the housing by connecting members, the collar having a central opening aligned with the lumen of the housing for passage of the medical device, and an annular surface which surrounds the opening and is operable to engage the annular surface of the housing to clamp tissue therebetween, and thereafter release the tissue by releasing the clamp.

2. The clamp of claim 1, wherein the connecting member comprises a plurality of struts.

3. The clamp of claim 2, wherein the struts are pivotally connected to the housing and the collar.

4. The clamp of claim 3, wherein the struts have a pivoting internal joint.

5. The clamp of claim 1, wherein the housing includes a plurality of distally extending slots.

6. The clamp of claim 5, wherein the struts are located and operate within the slots.

7. The clamp of claim 1, further comprising a medical device, wherein the medical device is a cannula which is received through the lumen of the housing and extends proximally through the opening of the collar.

8. The clamp of claim 1, wherein the lumen of the housing further includes a hemostatic valve.

9. The clamp of claim 1, wherein the housing has a length of 0.3–2.0 inches and an outer diameter of 0.4–1.0 inches, and wherein the collar has a length of 0.25–0.75 inches and an outer diameter of 0.4–1.0 inches.

10. A method for sealing body tissues during introduction of a medical device, comprising the steps of:

providing a clamp comprising a generally cone-shaped housing having a proximal end, a distal end, and a lumen therebetween, the proximal end of the housing having an annular surface which lies in a plane substantially perpendicular to the longitudinal axis of the lumen, the clamp further comprising a collar operably connected to the proximal end of the housing by a connecting member, the collar having an annular surface which operates to engage the annular surface of the housing;

making an incision in the tissue;

introducing the distal end of the housing through the incision and positioning the tissue against the annular surface of the housing;

operating the collar to engage the tissue against the annular surface of the collar, wherein the tissue clamped between the annular surface of the housing and the annular surface of the collar; and introducing a medical device through the lumen of the housing into the body.

11. The method of claim 10, wherein the connecting member comprises a plurality of struts.

12. The method of claim 10, wherein the tissue is the right atrium.

13. The method of claim 10, wherein the tissue is a vessel.

14. The method of claim 13, wherein the vessel is an artery.

15. The method of claim 13, wherein the artery is the aorta.

16. The method of claim 10, wherein the medical device is a cannula.

17. The method of claim 16, further comprising the step of delivering oxygenated blood to the patient through the cannula.

18. The method of claim 10, wherein the lumen of the housing further includes a hemostatic valve.

19. The method of claim 17, further comprising a steps of coronary artery bypass grafting surgery.

20. The method of claim 17, further comprising the steps of valve repair.

21. The method of claim 10, further comprising the step of releasing the collar to disengage the tissue.

22. The method of claim 21, further comprising the step of removing the housing from the incision.

* * * * *